United States Patent [19]

Frame et al.

[11] Patent Number: 4,737,480

[45] Date of Patent: Apr. 12, 1988

[54] PROCESS FOR THE OLIGOMERIZATION OF OLEFINS AND A CATALYST THEREOF

[75] Inventors: Robert R. Frame, Glenview; Tamotsu Imai, Mount Prospect, both of Ill.

[73] Assignee: UOP Inc., Des Plaines, Ill.

[21] Appl. No.: 25,136

[22] Filed: Mar. 12, 1987

Related U.S. Application Data

[63] Continuation-in-part of Ser. No. 843,540, Mar. 25, 1986, abandoned.

[51] Int. Cl.$^4$ .................................................. C07C 2/30
[52] U.S. Cl. ...................................... 502/117; 585/512; 585/521; 585/531
[58] Field of Search ................ 502/117; 585/512, 521, 585/531

[56] References Cited

U.S. PATENT DOCUMENTS

| | | | |
|---|---|---|---|
| 3,155,642 | 11/1964 | Duck et al. | 502/117 |
| 3,432,517 | 3/1969 | Neda et al. | 502/117 |
| 3,457,321 | 7/1969 | Hambling et al. | 502/117 |
| 3,465,056 | 9/1969 | Hambling et al. | 585/512 |
| 3,483,260 | 12/1969 | Hambling et al. | 585/512 |
| 3,483,269 | 12/1969 | Magoon et al. | 585/512 |
| 3,505,425 | 4/1970 | Jones et al. | 585/512 |
| 3,530,200 | 9/1970 | Glockner | 585/513 |
| 3,592,869 | 7/1971 | Cannell | 585/512 |
| 3,663,451 | 5/1972 | Hill | 585/512 |
| 4,032,590 | 6/1977 | Burnham | 585/512 |
| 4,613,580 | 9/1986 | Frame | 502/117 |

FOREIGN PATENT DOCUMENTS

| | | | |
|---|---|---|---|
| 7222206 | 2/1967 | Japan | 585/512 |
| 5024282 | 5/1973 | Japan | 585/512 |
| 1123474 | 8/1968 | United Kingdom | 585/516 |

Primary Examiner—Asok Pal
Attorney, Agent, or Firm—Thomas K. McBride; John F. Spears, Jr.; Raymond H. Nelson

[57] ABSTRACT

Olefinic feedstocks which contain catalyst contaminants or poisons such as sulfur-containing compounds may be oligomerized to a desired oligomer and configuration of the oligomer by utilizing a catalyst which is stable and will not deactivate due to the presence of the aforementioned poisons. The catalyst comprises a porous support which has been impregnated with a catalytically effective amount of a non-stoichiometric hydrogen and oxygen-containing iron group metal compound and a compound containing a metal of Group IVA of the Periodic Table. In addition, the catalyst composite will also contain in combination therewith, a catalytically effective amount of an alkyl aluminum compound and an aluminum alkoxy/aluminum halide compound.

18 Claims, No Drawings

PROCESS FOR THE OLIGOMERIZATION OF OLEFINS AND A CATALYST THEREOF

CROSS-REFERENCE TO RELATED APPLICATIONS

This application is a continuation-in-part of our co-pending application Ser. No. 843,540 filed Mar. 25, 1986, all teachings of which are incorporated herein by reference thereto, now abandoned.

BACKGROUND OF THE INVENTION

The oligomerization of olefins is known in the art, such oligomerization processes being effected by treating olefinic hydrocarbons with certain catalysts to obtain various oligomers which will find a useful function in the chemical art. One type of catalyst which may be employed for this particular type of reaction comprises a supported metal compound. For example, U.S. Pat. No. 3,562,351 discloses a method for dimerizing olefins utilizing a supported catalyst which has been prepared by impregnating a suitable support with a salt solution of a Group VIII metal followed by a heat treatment in an inert atmosphere at a temperature less than that which is required to form a metal oxide but which will form a complex on the surface of the solid support. Following this, the catalyst is activated by treatment with an organometallic compound. U.S. Pat. No. 3,483,269 describes a catalyst useful for oligomerizing lower olefins which comprises a $\pi$-allyl nickel halide supported on an acidic inorganic oxide support. If so desired, the support may have been optionally treated with an alkyl aluminum compound. U.S. Pat. No. 3,592,869 also describes a catalyst which is useful for the oligomerization of olefins. A divalent nickel compound and an alkyl aluminum compound are contacted with an olefinic compound. The resulting mixture is then used to impregnate an inorganic refractory oxide support. Another patent, namely U.S. Pat. No. 3,644,564, describes a catalyst for the oligomerization of ethylene which comprises an organo aluminum-free reaction product of a nickel compound which is an atom of nickel in complex with an olefinically unsaturated compound and a fluorine-containing ligand. The catalysts are typically formed in situ. U.S. Pat. No. 3,679,772 describes a process for reacting monoolefins with diolefins, the catalyst for such a reaction comprising a complex of (1) nickel, (2) a group VA electron donor liquid such as an organophosphine, (3) a nonprotonic Lewis acid and (4) a reducing agent which itself may be a Lewis acid, all of which are composited on an acidic silica-based support.

U.S. Pat. No. 3,697,617 describes an oligomerization process involving the use of a catalyst comprising a complex of nickel with a chloro-containing electron donor ligand such as chlorodiphenylphosphine combined with a nonprotonic Lewis acid which is capable of forming a coordination bond with nickel and a reducing agent capable of reducing nickel acetylacetonate to an oxidation state less than 2. This complex may be composited on a solid support comprising an acidic silica-based material such as silica-alumina. The Lewis acid and the reducing agent may comprise the same compound as, for example, ethyl aluminum sesquichloride. U.S. Pat. No. 3,663,451 describes a catalyst which is obtained by reacting a transition metal halide such as nickel halide with a carrier to give a carrier-metal bond. This product is then reacted with a ligand such as a phosphine or ketone and finally activated by treatment with an aluminum alkyl or chloro alkyl.

U.S. Pat. No. 3,755,490 describes the polymerization of an olefin utilizing a catalyst comprising nickel, a Group VA electron donor ligand, a Lewis acid, and a reducing agent on a solid acidic silica-based support. U.S. Pat. No. 3,954,668 is drawn to an oligomerization catalyst comprising a nickel compound, a chloro-containing electron donor ligand, or a phosphorous compound, a nonprotonic Lewis acid reducing agent which is capable of reducing nickel acetylacetonate to an oxidation state of less than 2 and which is also capable of forming a coordination bond with a nickel. U.S. Pat. No. 3,170,904 speaks to a catalyst which is useful for polymerization comprising a large surface area metal of Groups VIIA or VIII of the Periodic Table, boron trifluoride etherate, an organometallic compound of Groups I, II, III or IV or a halo derivative of an organometallic compound of Groups II, III or IV or a hydride of a metal of Groups I, II or III. The large surface area metal which comprises one component of this catalyst is in metallic form as, for example, Raney nickel. If so desired, the catalyst may be composited on a diatomaceous earth carrier. In like manner, U.S. Pat. No. 3,170,906 discloses a catalyst which comprises (A) a carrier-supported nickel or cobalt oxide which has been prepared by impregnating the carrier with the hydroxide, organic acid salt, inorganic acid salt, followed by oxidation in the presence of oxygen or a combination of nitrogen and oxygen; (B) a boron, titanium, zirconium, or vanadium halide; and (C) an alkyl metal or alkyl metal halide. In addition to these patents, British Patent No. 1,390,530 describes an oligomerization catalyst which has been prepared by thermally pretreating a metal oxide carrier material followed by reacting with a halogen-containing organoaluminum compound and thereafter in a step-wise fashion, impregnating this product with a divalent nickel or cobalt complex at temperatures ranging from $-50°$ to $150°$ C.

Several other patents which describe oligomerization or polymerization catalysts which are unsupported in nature or processes include Japanest Patent No. 5024282 which is drawn to a catalyst containing a Group VIII metal and tin chloride or zinc chloride as well as Japanese Patent No. 4722206 which describes an unsupported catalyst prepared by mixing a nickel compound, an aluminum organic compound and a tin tetrahalide. U.S. Pat. No. 3,155,642 describes an unsupported catalyst prepared from an alkyl tin compound and aluminum chloride in addition to a nickel or cobalt compound for the polymerization of a dienic compound. U.S. Pat. No. 3,155,642 also describes an unsupported catalyst comprising a nickel carboxylate, a halide of a metal of Group IV or V and an organoaluminum compound containing at least one alkoxy radical, said catalyst being used for the polymerization of cis-1,4- polybutadiene. Likewise, U.S. Pat. No. 3,457,321 describes an unsupported catalyst prepared from a complex organic compound of a metal of Group VIII, a reducing agent and a tin tetraalkyl compound. Furthermore, U.S. Pat. Nos. 3,483,268 and 3,505,425 are also drawn to unsupported catalysts, the former showing a catalyst comprising nickel acetyl acetonate, an organonickel compound, and an activating agent of an aluminum alkyl alkoxide or aluminum trialkyl while the latter is drawn to a process for preparing this catalyst. British Patent No. 1,123,474 likewise teaches a process for preparing linear dimers using a catalyst comprising a complex organaic compound of a metal of a Group VIII and a tin tetraalkyl compound.

It is to be noted again that each of the patents disclosed in the above paragraph are drawn to *unsupported* catalysts for use in dimerization or polymerization reactions using different starting materials in the preparation thereof in contradistinction to the supported catalyst of the present invention which is hereinafter more fully described as to composition and method of preparation as well as the use thereof.

As will hereinafter be shown in greater detail, the oligomerization of olefinic hydrocarbons to provide products which possess a desired configuration with respect to the branching or minimal branching of the resultant chain may be accomplished by treating said olefins in the presence of a catalyst of the present invention, this catalyst will maintain its activity and stability for a relatively long period of time in the presence of certain impurities or poisons in the feedstock.

BRIEF SUMMARY OF THE INVENTION

This invention relates to a catalytic composite which is useful for the oligomerization of olefinic hydrocarbons. More specifically, the invention is concerned with a catalyst composite and a process for the oligomerization of olefinic compounds, particularly olefinic hydrocarbons, whereby the use of the catalytic composite will result in the obtainment of selective oligomers of the olefinic feed stock.

The term "polymerization" has a relatively broad meaning in the chemical art. Although it is generally referred to as the preparation of relatively high molecular weight polymers, that is polymers possessing molecular weights of greater than 50,000 or more, it may also refer to low molecular weight polymers, that is, polymers possessing molecular weights lower than 50,000. In contradistinction to this, the term "oligomerization" refers to polymeric compounds in which the molecules consist of only a relatively few monomeric units and thus would include dimerization, trimerization or tetramerization.

Many olefinic hydrocarbons which contain from 4 to about 12 carbon atoms in the chain are utilized in various industries in many ways. For example, dimers of propylene, regardless of the amount of branching, may be used to improve the octane number of motor fuels which are utilized in internal combustion engines utilizing gasoline as the fuel thereof. The presence of these compounds in a motor fuel such as gasoline will improve the octane number of the fuel to a high level, thus enabling the gasoline to be utilized in combustion engines in an unleaded state. Other uses for dimers containing 6 carbon atoms would be in the synthesis of flavors, perfumes, medicines, dyes and resins. Another use of an oligomer would be found in the dimerization product of butene in which the dimer which possesses a relatively straight chain configuration with a minimum of branching such as one methyl substituent on the chain would be as an intermediate in the production of a plasticizer. The plasticizer, when added to a plastic, will facilitate compounding and improve the flexibility as well as other properties of the finished product. Likewise, a trimer of butene or a dimer of hexane in which the olefin contains 12 carbon atoms may be used as an intermediate in various organic syntheses such as in the preparation of detergents, lubricants, additives, plasticizers, flavors, perfumes, medicines, oil, dyes, etc. In addition, linearized oligomers containing 12 or more carbon atoms, upon hydrogenation, provide excellent diesel fuels.

It is therefore an object of this invention to provide a catalyst for the oligomerization of olefinic hydrocarbons.

A further object of this invention is to provide a specific catalyst stream which may be used in a process for the oligomerization of olefinic hydrocarbons whereby selective oligomers may be obtained as a result of this process.

In one aspect, an embodiment of this invention resides in a catalytic composite comprising a combination of a catalytically effective amount of an alkyl aluminum compound on a porous support containing a catalytically effective amount of a non-stoichiometric hydrogen and oxygen-containing iron group metal compound and a compound containing a metal of Group IVA of the Periodic Table.

Another embodiment of this invention is found in a process for the oligomerization of an olefinic hydrocarbon which comprises treating said hydrocarbon in the presence of a catalytic composite comprising a combination of an alkyl aluminum compound on a porous support containing a catalytically effective amount of a nonstoichiometric hydrogen and oxygen-containing iron group metal compound and a compound containing a metal of Group IVA of the Periodic Table at oligomerization conditions, and recovering the resultant oligomer.

A specific embodiment of this invention is found in a catalytic composite comprising a combination of a catalytically effective amound of diethyl aluminum chloride on an alumina-support containing a catalytically effective amount of a non-stoichiometric hydrogen and oxygen-containing nickel compound and stannic chloride.

Another specific embodiment of this invention is found in a process for the oligomerization of an olefinic hydrocarbon which comprises treating butene in the presence of a catalyst comprising a combination of a catalytically effective amount of diethyl aluminum chloride and a catalytically effective amount of tri-t-butoxy aluminum on an alimina support which contains a catalytically effective amount of a non-stoichiometric hydrogen and oxygen-containing nickel compound and stannic chloride, at a temperature in the range of from about −20° to about 200° C. and a pressure in the range of from about 350 to about 1,000 pounds per square inch gauge, and recovering the resultant oligomer comprising a mixture of octene, methylheptene and dimethylhexene.

Other objects and embodiments will be found in the following further detailed description of the invention.

DETAILED DESCRIPTION OF THE INVENTION

As hereinbefore set forth, the present invention is concerned with a catalyst composite which may be utilized for the oligomerization of olefins and to a process which employs the catalyst. Heretofore, the preparation of a catalytic composite which may be used for the polymerization or oligomerization of olefinic compounds was relatively difficult inasmuch as several relatively expensive compounds were required as components of the composite as well as entailing somewhat complicated methods for the manufacture thereof. In contradistinction to this, the catalytic composite of the present invention is relatively easy to prepare and, in addition, employs compounds which are less expensive than the components of the other catalyst. The final catalytic composite of the present invention will possess a high activity and will be stable over a relatively long period of time. Furthermore, the catalytic composite of the present invention will possess the desired stability and activity due to the ability of the catalyst to effect the desired oligomer reaction in spite of the presence of impurities which would, under ordinary circumstances, poison or deactivate the catalyst.

The particular impurities which are present in the feedstock and which act to deactivate the catalyst, comprise various sulfur compounds such as carbonyl sulfide, hydrogen sulfides; mercaptans such as methyl mercaptan, ethyl mercaptan, propyl mercaptan, etc.; disulfides such as dimethyl disulfide, diethyl sulfide, etc. In addition, other catalyst deactivating impurities such as oxygenates comprising oxygencontaining organic compounds such as alcohols, includiing methyl alcohol, ethyl alcohol, propyl alcohol, etc.; ethers such as di-methyl ether, diethyl ether, methyl ethyl ether, methyl propyl ether, etc.; aldehydes such as formaldehyde, acetaldehyde; and ketones such as acetone; methyl ethyl ketone, etc. Generally speaking, the impurities may be present in trace amounts such as in a range of from about 0.1 to about 100 ppm of feedstock. However, even these trace amounts of impurities will have a deleterious effect upon the activity and stability of the oligomerization catalysts and thus quickly deactivate the catalyst when these impurities are present.

We have now unexpectedly discovered that the novel catalysts of the present invention which are prepared according to the methods hereinafter set forth, will exhibit an unexpected resistance to the poisoning effect of the impurities and thus, will permit the catalyst to maintain a desired activity as well as being stable for a long period of time when employed in the conversion of olefinic hydrocarbons to desired dimers. In addition to these desired attributes, the catalyst will also produce a high yield of dimer products, especially from $C_3$ and $C_4$ olefins as compared to trimer and tetramer products. The dimer products produces by the oligomerization of propylene or the n-butenes will possess a high percentage of linear compounds, that is, n-hexenes and n-octenes and also a high percentage of dimers which contain only one methyl substituent; more highly branched oligomers being minority products. The propylene dimers which are produced by the process of the present invention all possess high octane numbers regardless of the branching, and thus are excellent octane blending components. In addition, the n-butene dimers are excellent as intermediates in the preparation of plasticizers.

The catalytic composite of the present invention will comprise a combination of a catalytically effective amount of an alkyl aluminum compound composited on a porous support containing a hydrate of an iron group metal salt and a compound containing a metal of Group IVA of the Periodic Table. In the preferred embodiment of the invention, the iron group metal hydrate will be obtained from a soluble salt of nickel or cobalt such as, for example, nickel nitrate, nickel hydroxide, nickel bromide, nickel chloride, nickel fluoride, nickel actate, cobaltic chloride, cobaltout acetate, cobaltous ammonium chloride, cobaltous bromide, cobaltous fluoride, cobaltout perchlorate, cabaltous sulfate, etc. The compound containing the Group IVA metal will comprise salts of these metals such as germanium chloride, germanium iodide, germanium fluoride, germanium sulfide, etc.; stannic bromide, stannic chloride, stannic oxychloride, stannic sulfate, lead acetate, lead perchlorate, etc. It is also contemplated within the scope of this invention that these metals may also be used in their elemental form as one component of the catalytic composite of the present invention.

The porous support upon which the iron group metal hydrate is impregnated will include inorganic metal oxides such as alumina, silica, mixtures of oxides such as alumina-silica, alumina-zirconiamagnesia, etc. or crystalline aluminosilicates which are commonly known as zeolites.

Examples of alkyl aluminum compounds which form another component of the catalytic composite will include alkyl aluminum halides such as dimethyl aluminum chloride, diethyl aluminum chloride, dipropyl aluminum chloride, diemethyl aluminum bromide, diethyl aluminum bromide, dipropyl aluminun bromide, diemethyl aluminum iodide, diethyl aluminum iodide, dipropyl aluminum iodide, etc.

Another component which may be present in the catalyst composite of the present invention will comprise an aluminum alkoxy compound which will act as an activator for the catalytic composite. Examples of these aluminum alkoxy compounds will possess the generic formula $Al(OR)_3$ in which R comprises a lower molecular weight alkyl radical containing from one to about six carbon atoms. Some specific examples of these aluminum alkoxy compounds will include trimethoxy aluminum, triethoxy aluminum, tripropoxy aluminum, triisopropoxy aluminum, tri-n-butoxy aluminum, tri-t-butoxy aluminum, tripentoxy aluminum, trihexoxy aluminum, etc. It is also contemplated within the scope of this invention that the catalytic composite may, if so desired, also contain an aluminum halide compound in place of the aluminum alkoxy compound or in conjunction therewith. Examples of these aluminum halide compounds will include aluminum chloride, aluminum bromide, aluminum iodide, etc. It is to be understood that the aforementioned list of iron group metal compounds, Group IVA metal compounds, alkyl aluminum compounds, and aluminum alkoxy compounds, are only representative of the class of compounds which may be employed to form the catalytic composite of the present invention, and that said invention is not necessarily limited thereto.

The oligomerization catalyst of the present invention may be prepared in such a manner so as to provide the finished catalyst with the desired characteristics with regard to the selectivity of olefins obtained by the reaction of an olefinic hydrocarbon in the presence of such catalysts, as well as specificity of the product so obtained. The catalyst composite may be prepared by impregnating a porous support of the type hereinbefore set forth with a simple divalent iron group metal salt such as, for example, nickel nitrate, and a Group IVA metal salt such as tin chloride, preferably from an aqueous solution. Alternatively, the porour support may be impregnated with an aqueous iron group metal salt and the Group IVA metal may be incorporated into the support by any techniques which are well known to those skilled in the art. For example, sols such as tin or germanium sols may be prepared and impregnated into the support by well-known sol/gel techniques. In any event, after impregnation of the porous support such as alumina, said impregnation being effected at ambient temperature and atmospheric pressure, the impregnated support is then subjected to a thermal treatment. By varying the temperature of the thermal treatment, it is possible to obtain a catalyst composite which will provide a greater selectivity to dimer products resulting from the oligomerization of the olefin which will be found to be present in greater amounts in contrast to trimer and tetramer products then are obtained when using other conventional oligomerization catalysts. The thermal treatment of the impregnated support is preferably effected in a range of from about 300° C. to about 450° C., the preferred thermal treatment temperature being in a range of from about 340° C. to about 360° C. The thermal treatment or calcination of the catalyst base containing the impregnated Group IVA metal or salt thereof and iron group metal salt in hydrate form will result in a weight loss due to a loss of water of hydration from the metal salt and will result in the formation of a non-stoichiometric hydrogen and oxygen-containing iron group metal compound which may also be referred to as a hydrate of an iron group metal salt. In the preferred embodiment of the invention, the mole ratio of water of hydration to iron group metal following the thermal treatment will be greater than 0.5:1 and preferably in a range of from about 0.5:1 to about 6:1. The thermal treatment of the catalyst base containing the iron group metal compound in the form of a hydrate will usually be effected for a period of time which is less than that requiried to completely drive off all of the water of hydration.

The thermal treatment or calcination of the catalyst base and the iron group metal salt as temperatures within the range hereinbefore set forth will result in a bonding of the iron group metal to the catalyst base usually by means of a metal-oxygen base bond, the oxygen portion of the bond being supplied in part by the hydroxyl groups which are present on the surface of the porous support of the type hereinbefore set forth in greater detail.

Following the thermal treatment, the iron group metal impregnated catalyst base is then treated with an alkyl aluminum compound and an aluminum alkoxy compound to produce a catalyst of maximum activity. The treatment of the base with the aluminum alkyl compound and the activator is also effected at ambient temperature and atmospheric pressure utilizing a solution of the two compounds dissolved in an organic solvent such as benzene, toluene, isomeric xylenes, etc.

The addition of the organic solution, or conversely the addition of the impregnated base to the organic solution, will result in an exothermic reaction and, after thorough admixture, the resulting solution containing the impregnated base is allowed to return to room temperature. The solvent may then be removed by conventional means such as decantation, evaporation, filtration, etc. and the catalyst composite may then be washed with an organic solvent to remove residue or trace portions of unwanted compounds. Thereafter, the catalyst may then be dried by purging with nitrogen, and recovered. In the finished composite, the alkyl aluminum compound is present in the composite in a mole ratio in the range of from about 0.05:1 to about 6:1, preferably in a range of from about 0.1:1 to about 1:1, moles of alkyl aluminum compound per mole of iron group metal, the latter being present in said composite, or an elemental basis, in an amount in the range of from about 1% to about 20% by weight of the composite, and preferably in an amount in a range of from about 1% to about 10%. In addition, the Group IVA metal will also be present in said composite, on an elemental basis, in an amount in the range of from about 0.1% to about 20% by weight of the composite, and preferably in an amount in the range of from about 1% to about 10%.

As will hereinafter be shown in greater detail, by preparing a catalyst which possesses the various components in the finished composite in mole ratios or weight percent within the ranges hereinbefore set forth, it is possible to selectively oligomerize olefin compounds containing from about 2 to about 6 carbon atoms with a concurrent obtention of desirable isomers in each of the oligomer products. In addition, by utilizing the presence of a metal of the Group IVA of the Periodic Table in the catalyst composite, as well as an aluminum alkoxide compound, it is possible to obtain a catalyst composite which will be more stable, in that it will not deactivate in the presence of the type of impurities hereinbefore set forth in greater detail which may themselves be present in the feedstock, and which may impede or deter the oligomerization reaction of the present invention.

As an example of how the catalyst composite of the present invention may be prepared, a predetermined amount of a porous base such as alumina, silica, silica-alumina, aluminosilicate, etc. which may be in the form of spheres, pellets, rods, etc. may be prepared in an appropriate apparatus such as an evaporator along with an aqueous solution of a hydrate of an iron group metal salt and a Group IVA metal salt. The mixture may be thoroughly admixed and following this, the apparatus heated to form the desired iron group metal and Group IVA metal impregnated base. The impregnated base may then be placed in a heating apparatus such as a tube furnace and treated with air while bringing the catalyst to a temperature of about 250° C. The heating is accomplished at a relatively slow rate and after the determined temperature has been reached, it is maintained thereat for an additional period of time which may range from about 2 to about 4 hours or more in duration. The calcination of the catalyst base is then effected by increasing the temperature to a predetermined level and maintaining thereat for a period of time sufficient to bring the mole ratio of water of hydration present in the iron group metal salt to a determined level which is preferably in an excess of about 0.5:1 moles of water of hydration per mole of iron group metal.

After allowing the calcination to proceed for this predetermined period of time, heating is discontinued and the catalyst base which contains from about 1% to about 20% by weight of iron group metal and from about 0.1% to about 20% by weight of Group IVA metal, is allowed to cool. The cooled base may then be admixed with a solution of an alkyl aluminum compound and an aluminum halide/aluminum alkoxy compound dissolved in an organic solvent. As previously discussed, the resulting reaction is exothermic in nature and after allowing the heat to dissipate, the resulting admixture is thoroughly stirred and allowed to stand for a period of time which may range from about 1 to about 100 hours or more in duration. At the end of this period, the organic solvent is removed by decantation, filtration, centrifugation, etc. and the solid catalyst is washed to remove any unreacted material. After washing, the catalyst is then dried in an inert atmosphere such as that provided for by the presence of nitrogen, and recovered.

The oligomerization of olefins containing from 2 to about 6 carbon atoms such as ethylene, propylene, butene-1, butene-2, pentene-1, pentene-2, pentene-3 may then be effected by treating the oligomer in the presence of the catalyst at oligomerization conditions which will include a temperature in the range of from about $-20°$ C. to about 200° C., the preferred range being from about 30° C. to about 100° C., and a pressure in the range of from about 350 to about 1,000 pounds per square inch gauge (psig). The pressure which is utilized may be the autogenous pressure provided for by the feedstock, if in gaseous phase, or the feedstock may supply only a partial pressure, the remainder of said pressure being provided by the introduction of an inert gas such as nitrogen, helium, argon, etc. into the reaction zone.

It is contemplated within the scope of this invention that the oligomerization process may be effected in either a batch or continuous type operation. For example, when a batch type operation is employed, a quantity of the novel catalyst composite of the present invention may be placed in an appropriate apparatus such as, for example, an autoclave of the rotating, mixing or stirring type. If the olefinic feedstock is in gaseous form, the autoclave is sealed and the feedstock comprising the olefinic hydrocarbon or a mixture of olefinic and paraffinic hydrocarbon or similar carbon atom length is charged to the reactor until the desired operating pressure has been attained. The apparatus is then heated to the desired operating temperature and maintained thereat for a predetermined period of time which may range from about 1 to about 6 hours or more in duration. At the end of this period of time, heating is discontinued and after the apparatus and contents thereof have returned to room temperature, the excess pressure is discharged and the autoclave is opened. The reaction product is recovered, separated from the catalyst by conventional means such as decantation, filtration, centrifugation, etc. and, if so desired, subjected to fractional distillation whereby the various isomers may be separated, one from another, and stored. Conversely, if so desired, the reaction product comprising a mixture of isomers may be recovered and stored per se without separating the various isomeric fractions which are present in the product mixture.

In the event that the olefinic charge stock is in liquid form, it may be charged to the reactor which is thereafter sealed and pressured to the desired operating pressure by the introduction of an inert gas of the type hereinbefore set forth. The remainder of the operating pressure to obtain the desired oligomer product is carried out in a manner similar to that previously described.

When utilizing a continuous method of operation to obtain the desired oligomer products, a quantity of the catalyst composite is placed in an appropriate apparatus. The feedstock comprising the olefinic compound is continuously charged to this reactor which is maintained at the proper operating conditions of temperature and pressure. As in the case of the batch type operation, the desired operating pressure may be provided for by the olefinic hydrocarbon itself or by the addition of a heated inert gas. After passage through the reactor for a predetermined period of time, the reactor effluent is continuously discharged and the reaction product may be recovered and passed to storage or it may be passed to a distillation apparatus whereby separation of the various isomers and oligomers may be effected. Any unreacted olefinic hydrocarbon which is recovered from the reactor effluent may be recycled back to the reactor to form a portion of the feed charge.

Inasmuch as the catalyst composite of the present invention is in solid form, the continuous method of operation for obtaining the desired oligomers of the olefinic hydrocarbons may be effected in various types of operations. For example, in one type of operation, the catalyst is positioned as a fixed bed in the reaction zone and the olefinic feedstock is charged so that it passes over the catalyst bed in either an upward or downward flow. Another type of continuous operation which may be employed comprises the moving bed type of operation in which the catalyst bed and the feedstock are passed through the reaction zone either concurrently or countercurrently to each other. In addition to the fixed or moving bed type of operation, it is also contemplated that the slurry type of operation may be employed, especially when the olefinic hydrocarbon feedstock is in liquid form. When this type of operation is employed, the catalyst is charged to the reactor as a slurry in the olefinic feedstock.

Examples of oligomers of olefinic compounds which may be obtained when utilizing the catalyst composite of the present invention will include n-butene, isobutene, n-hexene, methyl pentene, dimethyl butene, n-octene, the isomeric heptenes, dimethyl hexenes, n-dodecene, the isomeric methyl undecenes, dimethyl decenes, etc. As was previously stated, the oligomer products which are obtained in the process of this invention will comprise, in the main, the dimers of the particular olefinic compound which was employed as the feedstock, thus, for example, when employing ethylene as the feed, the reaction product will comprise mostly $C_4$ olefins; when employing propylene as the feedstock, the reaction product will comprise mostly $C_6$ olefins; and when employing butene as the feedstock, the reaction product will comprise mostly $C_8$ olefins. Thus, the catalyst composite of the present invention will result in products which find particular uses in the finished product.

The following examples are given for purposes of illustration the novel catalyst composites of the present invention, methods for preparing these composites and a process for utilizing these composites. However, it is to be understood that these examples are merely illustrative in nature and that the present invention is not necessarily limited thereto.

EXAMPLE I

A catalyst was prepared by impregnating 250 cc of ⅛" alumina spheres with an aqueous solution of nickel nitrate hexahydrate. The impregnation was effected in a steam-jacketed rotary evaporator in which the mixture was rolled for a period of 0.5 hours at ambient temperature. The evaporator was then heated with steam for a period of 2 hours during which time the water phase was evaporated. Following this, the nickel nitrate impregnated alumina base was loaded into a tube furnace and a flow of air was established, the air passing through the catalyst bed at a rate of 600 cc per minute. The catalyst was brought to a temperature of 250° C. and maintained thereat for a period of 3 hours. Thereafter, the temperature was increased to 400° C. and maintained thereat for an additional period of 2 hours. Following this, heating was discontinued and the impregnated catalyst base, containing 5.5 wt. % of nickel, was recovered.

After cooling the impregnated alumina, it was then activated by adding 7.3 grams of diethyl aluminum chloride and 2.9 grams of trisec-butoxy aluminum per 100 cc of support in a toluene solution, the activation of the alumina base being effected in a glove box under a nitrogen atmosphere. The addition of the activator was accomplished by slowly adding the activator solution over a period of 15 minutes to the catalyst base, heat being evolved during this addition due to the exothermic nature of the reaction. After completion of the addition of the activator solution, the flask was intermittently swirled over a period of 12 hours. At the end of the 12 hour period, the solvents were decanted and the catalyst composite was washed with 6 portions of isopentane utilizing 100–115 cc per wash. The resulting catalyst composite was then allowed to dry by evaporation of the excess isopentane while maintaining an atmosphere of nitrogen in the glove box.

EXAMPLE II

In this example, a catalyst composite of the present invention was prepared by impregnating a catalyst base of ⅛" spheres with an aqueous solution of nickel nitrate hexahydrate and stannic chloride pentahydrate, the impregnation of the base with the aqueous solution being accomplished in a manner similar to that hereinbefore set forth in Example I. The water present was evaporated by use of a steamjacketed rotary evaporator.

The nickel nitrate/tin chloride containing alumina base was placed in a tube furnace under a flow of air and calcined at a temperature of 250° C. for a period of 3 hours, followed by a calcination at 400° C. for a period of 2 hours. The finished calcined support contained 4.5 wt. % nickel and 1.8 wt. % tin after calcination.

The activation of the catalyst base was effected by placing said base covered with toluene in an Erlenmeyer flask in a glove box, a toluene solution of diethyl aluminum chloride and tri-sec-butoxy aluminum was slowly added during a period of 15 minutes to prevent overheating of the catalyst base due to evolution of heat involved in the exothermic reaction. The weights of the activating compounds per 100 cc of support were 2.9 grams of tri-sec-butoxy aluminum and 7.3 grams of diethyl aluminum chloride. After intermittently swirling the flask during a period of 12 hours, the toluene was decanted and the catalyst composite was washed with 6 portions of isopentane. Thereafter the catalyst composite was allowed to dry in a glove box under a nitrogen atmosphere until it was free-flowing in nature.

EXAMPLE III

The catalyst which was prepared in accordance with Example I above was utilized in the oligomerization of a butene feed, said feedstock comprising a mixture of 60% butene and 40% n-butene which also contained 30 ppm by weight of dimethyl disulfide and 45 ppm by weight of methyl t-butyl ether. The oligomerization was effected by placing 50 cc of the catalyst in a tubular reactor having a ½" inner diameter. The feedstock was charged downflow to the reactor at an LHSV of 2.0 hours$^{-1}$ while maintaining reaction conditions which included an inlet temperature of 70° C. and a pressure of 700 psig. Feedstock was charged to the reactor only for a period of 12 hours. During this time the catalyst bed maximum temperatue was never more than 1.3° C. above the inlet temperature. Oligomerization is a strongly exothermic reaction and during runs wherein high n-butene conversions are observed, much higher catalyst bed maximum temperatures are observed. The average n-butene conversion over the 12 hour run calculated from the n-butene/n-butane compositions of the feed and the product was only 10 wt. % (Table 1).

Only a small amount of $C_{4+}$ liquid was collected. It had the properties in Table 1.

By the end of 12 hours, the small exotherm had moved down the bed as is characteristic of a catalyst deactivation due to a feed poison.

TABLE 1

| HOURS | BUTENE CONVERSION % | SELECTIVITY $C_8$ = WT. % | $C_8$ = Isomer Distribution % | | |
|---|---|---|---|---|---|
| | | | N—OCTENE | METHYL HEPTENE | DIMETHYL HEXENE |
| 0–12 | 10.0 | 89.2 | 10.9 | 64.6 | 24.5 |

EXAMPLE IV

To illustrate the efficacy of the catalyst of the present invention in which the alumina base was impregnated with both nickel and tin with regard to its ability to remain stable and active in the presence of impurities which normally act as poisons to the catalyst, a second run was made. In this run, 50 cc of the catalyst of the present invention which was prepared according to Example II above, were placed in a tubular reactor similar in nature to that described in the above example. The conditions which were employed in this oligomerization reaction were similar to those utilized in Example III, that is, a feedstock of 60% butene and 40% n-butane which contains 30 ppm by weight of dimethyl disulfide and 45 ppm by weight of methyl t-butyl ether, was charged to the reactor at an LHSV of 2.0 hrs$^{-1}$, while maintaining an inlet temperature of 70° C. and a pressure of 700 psig. The reaction was allowed to proceed for a period of 92 hours, samples being taken intermittently during this period and analyzed by gas chromatography. The results of these analyses are set forth in Table 2 below:

TABLE 2

| HOURS | BUTENE CONVERSION % | SELECTIVITY $C_8$ = WT. % | $C_8$ = Isomer Distribution % | | |
|---|---|---|---|---|---|
| | | | N—OCTENE | METHYL HEPTENE | DIMETHYL HEXENE |
| 0–12 | 71.0 | 84.4 | 10.4 | 64.7 | 24.9 |
| 13–24 | 67.4 | 85.8 | 10.6 | 64.9 | 24.5 |
| 25–36 | 62.5 | 87.3 | 11.5 | 64.5 | 24.0 |
| 37–48 | 48.9 | 86.6 | 12.0 | 64.7 | 23.3 |

TABLE 2-continued

| HOURS | BUTENE CONVERSION % | SELECTIVITY $C_8=$ WT. % | $C_8=$ Isomer Distribution % | | |
|---|---|---|---|---|---|
| | | | N—OCTENE | METHYL HEPTENE | DIMETHYL HEXENE |
| 61–72 | 38.1 | 87.2 | 13.4 | 65.0 | 21.6 |

It is evident from a comparison of the results obtained, that utilizing a catalyst of the present invention as compared to a catalyst which does not contain a Group IVA metal as exemplified by tin, results in superior performance with regard to stability and activity.

We claim as our invention:

1. A catalytic composite for the oligomerization of olefins comprised of a catalytically effective amount of an alkyl aluminum compound on a porous support containing a catalytically effective amount of an iron group metal and a metal of Group IVA of the Periodic Table, said catalyst prepared by the steps of impregnating a porous support with an aqueous solution of an iron group metal salt and a Group IVA metal salt, calcining said impregnated support at a temperature in the range of from about 300° to 450° C., and contacting said calcined support with a solution comprised of an alkyl aluminum compound.

2. The catalytic composite as set forth in claim 1 in which said iron group metal is present in said composite, on an elemental basis, in an amount in the range of from about 1% to about 20% by weight of said composite.

3. The catalytic composite as set forth in claim 1 in which said alkyl aluminum compound is present in said composite in a mole ratio of alkyl aluminum compound to iron group metal in the range of from about 0.05:1 to about 6:1 moles.

4. The catalytic composite as set forth in claim 1 in which the weight ratio of Group IVA metal to iron group metal is in a range of from about 0.1:1 to about 10:1.

5. The catalytic composite as set forth in claim 1 in which said iron group metal is iron.

6. A catalytic composite as set forth in claim 1 in which said iron group metal is nickel.

7. A catalytic composite as set forth in claim 1 in which said Group IVA metal is tin.

8. The catalytic composite as set forth in claim 1 in which said Group IVA metal is germanium.

9. The catalytic composite as set forth in claim 1 in which said alkyl aluminum compound is dimethyl aluminum chloride.

10. The catalytic composite as set forth in claim 1 in which said alkyl aluminum compound is diethyl aluminum chloride.

11. The catalytic composite as set forth in claim 1 wherein said calcined support is additionally contacted with an aluminum alkoxy compound.

12. The catalytic composite as set forth in claim 11 in which said aluminum alkoxy compound is tri-t-butoxy aluminum.

13. The catalytic composite as set forth in claim 11 in which said aluminum alkoxy compound is tri-sec-butoxy aluminum.

14. The catalytic composite as set forth in claim 1 in which said porous support comprises alumina.

15. The catalytic composite as set forth in claim 1 in which said porous support comprises silica.

16. The catalytic composite as set forth in claim 1 wherein said calcined support is additionally contacted with an aluminum halide.

17. The catalytic composite as set forth in claim 16 in which said aluminum halide is aluminum chloride.

18. The catalytic composite as set forth in claim 16 in which said aluminum halide is aluminum bromide.

* * * * *